United States Patent
Jónsson et al.

(10) Patent No.: US 9,269,987 B2
(45) Date of Patent: Feb. 23, 2016

(54) ANIONS AND DERIVED SALTS WITH HIGH DISSOCIATION IN NON-PROTOGENIC SOLVENTS

(71) Applicants: Erlendur Jónsson, V. Frölunda (SE); Michel Bernard Armand, Paris (FR); Jens Patrik Johansson, Göteborg (SE)

(72) Inventors: Erlendur Jónsson, V. Frölunda (SE); Michel Bernard Armand, Paris (FR); Jens Patrik Johansson, Göteborg (SE)

(*) Notice: Subject to any disclaimer, the term of this patent is extended or adjusted under 35 U.S.C. 154(b) by 123 days.

(21) Appl. No.: 14/357,601

(22) PCT Filed: Nov. 16, 2012

(86) PCT No.: PCT/EP2012/072858
§ 371 (c)(1),
(2) Date: May 12, 2014

(87) PCT Pub. No.: WO2013/072470
PCT Pub. Date: May 23, 2013

(65) Prior Publication Data
US 2014/0272601 A1    Sep. 18, 2014

Related U.S. Application Data

(60) Provisional application No. 61/560,942, filed on Nov. 17, 2011.

(51) Int. Cl.
*H01M 10/0568* (2010.01)
*H01M 10/0565* (2010.01)
(Continued)

(52) U.S. Cl.
CPC ......... *H01M 10/0569* (2013.01); *C07D 213/02* (2013.01); *C07D 233/84* (2013.01); *H01M 4/13* (2013.01); *H01M 4/36* (2013.01); *H01M 4/485* (2013.01); *H01M 4/505* (2013.01);
(Continued)

(58) Field of Classification Search
CPC .................... H01M 10/0568; H01M 10/0565; H01M 10/0569; H01M 4/36; H01M 4/13; H01M 6/166; C07D 233/84; C07D 213/02; Y02E 60/122
See application file for complete search history.

(56) References Cited

U.S. PATENT DOCUMENTS

| 6,120,696 A | 9/2000 | Armand et al. ............. 252/62.2 |
| 6,171,522 B1 | 1/2001 | Michot et al. ................ 252/500 |

(Continued)

FOREIGN PATENT DOCUMENTS

| EP | 0 850 932 A1 | 7/1998 |
| EP | 2 380 882 A1 | 10/2011 |
| WO | WO 99/05100 | 2/1999 |

OTHER PUBLICATIONS

Tersac, G. "Etude Physiochimique de la Dihydroxy-3, 5 Pyridine et des Acides Hydroxypyridinesulfoniques Obtenus par Fusion Alcaline du Pyridinedisulfonate-3,5 de Potassium" Journal de Chimie Physique 1982 79(3):265-270.

(Continued)

*Primary Examiner* — Brittany Raymond
(74) *Attorney, Agent, or Firm* — Licata & Tyrrell P.C.

(57) ABSTRACT

Salts with formula $X^-M^+$ wherein $M^+$ is Li, Na, K, an ammonium, a phosphonium, an imidazolium, a pyridinium, or a pyrazolium and $X^-$ is an anion formed from covalent linking of two negative moieties to a positive onium-type core are provided. Also provided are electrolytes and batteries produced from these salts.

9 Claims, 1 Drawing Sheet

(51) Int. Cl.
  *H01M 10/0569* (2010.01)
  *H01M 4/36* (2006.01)
  *C07D 233/84* (2006.01)
  *C07D 213/02* (2006.01)
  *H01M 4/13* (2010.01)
  *H01M 4/485* (2010.01)
  *H01M 4/505* (2010.01)
  *H01M 4/525* (2010.01)
  *H01M 6/16* (2006.01)

(52) U.S. Cl.
  CPC ............ *H01M 4/525* (2013.01); *H01M 6/166* (2013.01); *H01M 10/0565* (2013.01); *H01M 10/0568* (2013.01); *Y02E 60/122* (2013.01)

(56) References Cited

U.S. PATENT DOCUMENTS

| | | | |
|---|---|---|---|
| 6,228,942 B1 | 5/2001 | Michot et al. | 525/183 |
| 6,319,428 B1 | 11/2001 | Michot et al. | 252/500 |
| 6,333,425 B1 | 12/2001 | Michot et al. | 558/167 |
| 6,340,716 B1 | 1/2002 | Armand et al. | 522/31 |
| 6,365,068 B1 | 4/2002 | Michot et al. | 252/500 |
| 6,395,367 B1 | 5/2002 | Michot et al. | 428/64.8 |
| 6,506,517 B2 | 1/2003 | Michot et al. | 429/213 |
| 6,548,567 B2 | 4/2003 | Armand et al. | 522/31 |
| 6,576,159 B1 | 6/2003 | Michot et al. | 252/511 |
| 6,835,495 B2 | 12/2004 | Michot et al. | 429/188 |
| 6,841,638 B2 | 1/2005 | Armand et al. | 526/240 |
| 7,378,034 B2 | 5/2008 | Armand et al. | 252/62.2 |
| 7,906,235 B2 | 3/2011 | Michot et al. | 429/199 |
| 2001/0024749 A1 | 9/2001 | Michot et al. | 429/122 |
| 2002/0009650 A1 | 1/2002 | Michot et al. | 429/314 |
| 2002/0013381 A1 | 1/2002 | Armand et al. | 522/31 |
| 2002/0102380 A1 | 8/2002 | Michot et al. | 428/64.8 |
| 2003/0052310 A1 | 3/2003 | Michot et al. | 252/500 |
| 2003/0066988 A1 | 4/2003 | Michot et al. | 252/500 |
| 2003/0195269 A1 | 10/2003 | Armand et al. | 522/31 |
| 2004/0162362 A9 | 8/2004 | Armand et al. | 522/31 |
| 2005/0074668 A1 | 4/2005 | Michot et al. | 429/199 |
| 2005/0123831 A1 | 6/2005 | Michot et al. | 429/188 |
| 2005/0158631 A1 | 7/2005 | Armand et al. | 429/307 |
| 2007/0205388 A1 | 9/2007 | Armand et al. | 252/62.2 |

OTHER PUBLICATIONS

International Search Report from PCT/EP2012/072858, Feb. 15, 2013, PCT.
International Preliminary Report on Patentability from PCT/EP2012/072858, May 20, 2014, PCT.

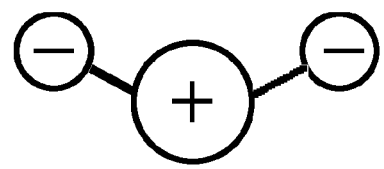

ANIONS AND DERIVED SALTS WITH HIGH DISSOCIATION IN NON-PROTOGENIC SOLVENTS

This patent application is the U.S. National Stage of International Application No. PCT/EP2012/072858 filed Nov. 16, 2012, which claims the benefit of priority from U.S. Provisional Application Ser. No. 61/560,942, filed Nov. 17, 2011, each of which are herein incorporated by reference in their entirety.

BACKGROUND OF THE INVENTION

In solvents, either a non-protogenic, often referred to as "aprotic", liquid or polymers bearing polar groups such as ethers, esters or nitriles, there is no solvation of the negative $X^-$ charge when attempting to induce ion conduction, i.e. forming an electrolyte, by dissolving a salt $X^-M^+$ in such media. Solubility then dissociation of the ion pair $X^-M^+$ is thus only effective when the anion $X^-$ does not require stabilization by forming hydrogen bonds, as in water, alcohols or amides RCONHR' where R or R'=H, an organic radical. Thus the main anions used in practice are $ClO_4^-$, $BF_4^-$, $PF_6^-$, $AsF_6^-$, $SbF_6^-$, $R_fSO_3^-$, $[(R_fSO_2)_2N]^-$, and $(R_fBF_3)^-$ where $R_f=C_nF_{2n+1}$, $(0 \geq n \geq 8)$. Another family of anions are the so-called "Hückel anions", such as 2-trifluoromethyl-4,5-dicyano-imidazole.

A main driving force for designing new anions is in the field of lithium batteries, in particular for highly conductive electrolytes where the polarizing lithium $M^+=Li$ is the countercation. The electrolyte in lithium batteries is subjected to extreme oxidizing conditions on the positive electrode side and extreme reducing conditions on the negative electrode side. $ClO_4^-$ leads to explosive mixtures with organic solvents and polymers; $BF_4^-$ and $R_fSO_3^-$ lead to a poorly conductive solution due to ion pairing; and $AsF_6^-$ and $SbF_6^-$ have as a core a heavy, highly toxic element. $[(R_fSO_2)_2N]^-$ or its higher homologues $\{CF_3SO_2N[S(O)(CF_3)N]_nSO_2CF_3\}^-$ are resistant to oxidation, but they do not passivate aluminum which is the only affordable positive electrode current collector. Most lithium batteries use $LiPF_6$ as a solute, which is far from satisfactory mainly since the salt has a propensity to equilibrate as $LiPF_6 \leftrightarrows LiF+PF_5$, the latter being a highly reactive Lewis acid, progressively destroying the solvent undergoing carbocationic chemistry. Another problem with all the salts containing fluorine is the release of highly toxic HF in the case of fire, an incident that occurs presently at a rate of a few ppm/cell, unacceptable for large scale applications, like electric road transportations. Presently, it has been impossible to avoid using fluorine, the most electronegative element, to impart resistance to oxidation to the anions. For instance the Bis(oxalatoborate) anion $\{[(C_2O_4)_2]B\}^-$ evolves $CO_2$ above 4 Volts vs. $Li^+:Li°$.

SUMMARY OF THE INVENTION

An aspect of the present invention relates to a salt of formula $X^-M^+$, wherein $M^+$ is selected from Li, Na, K, an ammonium, a phosphonium, an imidazolium, a pyridinium, a pyrazolium and wherein $X^-$ is an anion formed from covalent linking of two negative moieties to a positive onium-type core.

Another aspect of the present invention relates to electrolytes comprising these salts.

Yet another aspect of the present invention relates to batteries comprising electrolytes of these salts.

BRIEF DESCRIPTION OF THE FIGURES

FIG. 1 provides a diagram of an onium cation flanked by two negatively charged groups covalently attached to this central moiety.

DETAILED DESCRIPTION OF THE INVENTION

The present invention provides salts of formula $X^-M^+$, wherein $M^+$ is selected from Li, Na, K, an ammonium, a phosphonium, an imidazolium, a pyridinium, a pyrazolium and wherein $X^-$ is an anion formed from covalent linking of two negative moieties to a positive onium-type core. The present invention also provides electrolytes and batteries comprising these salts.

To overcome shortcomings of conventional salts, which are all based on the principle of delocalization of the negative charge on the largest possible number of atoms, the anion of a salt of the present invention is formed from an onium-type cation flanked by two negatively charged groups covalently attached to this central moiety, as depicted in the FIG. 1. These anions thus have a partially delocalized charge, but are also akin to zwitterions which are a single negative charge tethered to an organic cation, in the featured distinct positive and negative regions. As the charge is neither fully delocalized nor fully localized to a single region, the term "pseudo-delocalized" will henceforth be used to describe these anions.

The negative charges of the anion of the salt of the present invention can be selected from, but are not limited to, carboxylates, $-CO_2^-$, sulfonates $-SO_3^-$, alkoxides $-O^-$, thiolates $-S^-$, $-CO(NCN)^-$, $-CO[C(CN)_2)]^-$, $-SO_2(NCN)^-$, and $-SO_2[C(CN)_2)]^-$.

The positive onium-type central core of the anion of the salt of the present invention can be selected from, but is not limited to, ammonium, phosphonium, pyridinium, imidazolium, pyrazolium, and sulfonium.

The linkage between the two negative charges and the positive core of the anion can be a direct covalent bond or dative bond, or an alkylene link of 4 carbons or less.

In one embodiment of the present invention, the pseudo-delocalized anion of the salt of the invention is selected from, but not limited to:

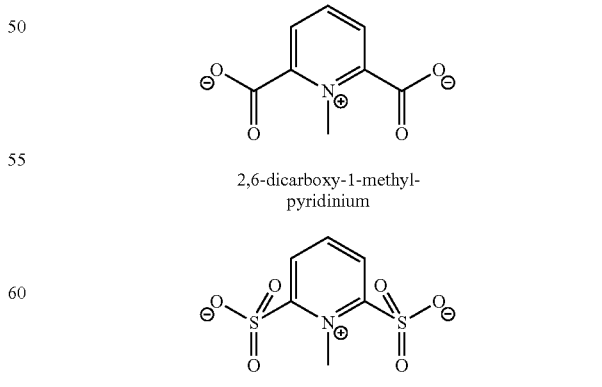

2,6-dicarboxy-1-methyl-pyridinium 2,6-disulfonato-1-methyl-pyridinium

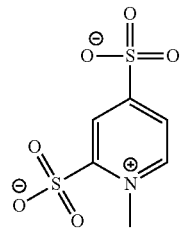

1,4-disulfonato-1-methyl-
pyridinium

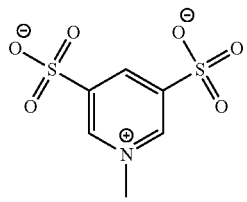

3,5-disulfonato-1-methyl-
pyridinium

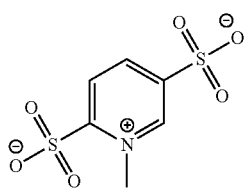

1,5-disulfonato-1-methyl-
pyridinium

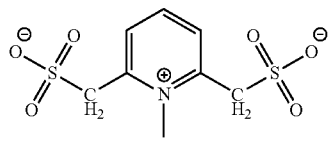 [SMILES: C[n+]1c(CS(=O)(=O)[O-])cccc1CS(=O)(=O)[O-]]

2,6-bis(sulfonato-methyl)-1-
methyl-pyridinium

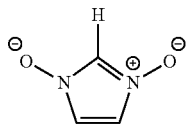

1,3 dioxyimidazolium

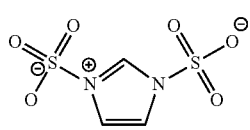

1,3 sulfonatoimidazolium

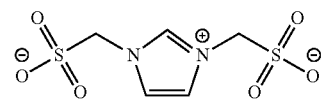 [SMILES: O=S(=O)([O-])Cn1cc[n+](CS(=O)(=O)[O-])c1]

1,3-bis(sulfonato-methyl)-
imidazolium

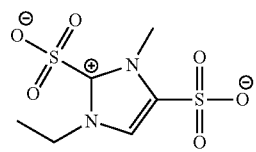 [SMILES: CCn1cc(S(=O)(=O)[O-])n(C)[c+]1S(=O)(=O)[O-]]

1-ethyl-2 methyl-2,4-bis
sufonatoimidazolium

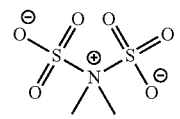

bis-sulfonato-dimethyl
ammonium

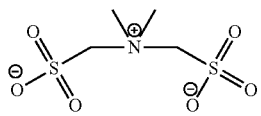

bis(sulfonato-methyl)-
dimethyl ammonium

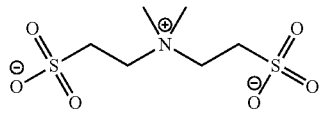

bis(sulfonato-2-ethyl)-
dimethyl ammonium

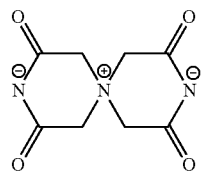 [SMILES: O=C1C[N+]2(CC(=O)[N-]1)CC(=O)[N-]C(=O)C2]

spiro-3,5,3'5'tetraoxa-4,4'
diaza-bis-piperidinium

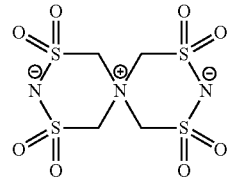 [SMILES: O=S1(=O)C[N+]2(CS(=O)(=O)[N-]1)CS(=O)(=O)[N-]S(=O)(=O)C2]

spiro-3,5,3',5'tetrathia-4,4'
diaza-bis-piperidinium,
3,5,5,5' octaoxide

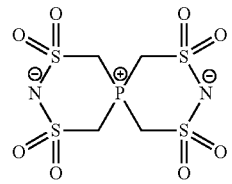 [SMILES: O=S1(=O)C[P+]2(CS(=O)(=O)[N-]1)CS(=O)(=O)[N-]S(=O)(=O)C2]

spiro-3,5,3',5'tetrathia-4,4'
diaza-bis-phospha-
piperidinium, 3,5,5,5'
octaoxide -continued

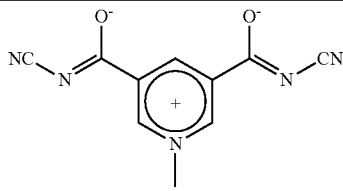

N,N'-dicyano-1-methyl-
pyridinium-3,5
dicarboxamide

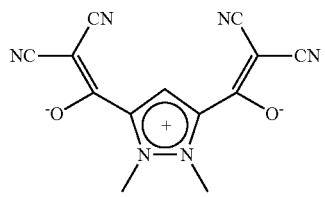

3,5-(dimalono-carbonyl)-
1,2-dimethyl-pyrazolium

The salts of the present invention are useful in electrolytes. Such electrolytes comprise the salt dissolved in a polar solvent, a solvating polymer or a mixture thereof. Examples of polar solvents which can be used in the electrolytes include, but are not limited to, linear and cyclic carbonates, ethers including mono-, di-, tri- and tetra-ethylene glycol di-methyl ether, tetrahydrofurane, □-butyrolactone, vinylene carbonate, tetraalkyl sulfonamides, and mixtures thereof. Examples of solvating polymers which can be used in the electrolytes include, but are not limited to, poly(ethylene oxide), polyacrylamide, poly(ethylene glycol) diacrylate or dimethacrylate, poly(methoxy ethylene glycol) monoacrylate or methacrylate, their random or block polymers with styrene, and a polyether comprising at least 60% of oxyethylene units.

These electrolytes are useful in lithium batteries. Such batteries comprise at least one positive electrode and at least one negative electrode, with the electrolyte comprising a salt of the present invention and further containing lithium or sodium ions. In one embodiment, the negative electrode of the lithium battery comprises metallic lithium, a lithium intercalation derivative of soft or hard carbons, graphite, a lithium-aluminum alloy, a lithium silicon alloy or $Li_4Ti_5O_{12}$. In another embodiment, the negative electrode comprises sodium, a sodium intercalation derivative of hard carbons, a sodium-lead alloy or $Na_{2+q}Ti_3O_7$ wherein $0 \leq q \leq 2$. In one embodiment, the positive electrode of the lithium battery comprises $LiFe_{1-x}Mn_xPO_4$ wherein $0 \leq x \leq 1$, $LiFeSO_4F$, $Li_yMn_2O_4$ wherein $0 \leq y \leq 1$, $Li_zCoO_2$ wherein $0 \leq z \leq 0.6$ or mixtures thereof. In another embodiment, the positive electrode comprises $Na_rFePO_4$, $(0 \leq r \leq 1)$ or $Na_{2-s}FePO_4F$ $(0 \leq s \leq 1)$ or $Na_{1-t}MnO_2$ $(0 \leq t \leq 1)$ and mixtures thereof.

The following nonlimiting examples are provided to further illustrate the present invention.

EXAMPLES

Example 1

To 1.34 g of imidazole in suspension in heptane is added 1 ml of 2M butyllithium in hexane and the mixture is stirred at room temperature for 24 hours. To this suspension, are added 3.2 g of sulfur trioxide in dichloromethane. The slurry is stirred further for 24 hours and the solids are separated by centrifugation to yield lithium [1,3 disulfonatoimidazolium].

Example 2

Pyridine-3,5-disulfonic acid is made from 3,5-dichloro-pyridine which is transformed into 3,5-dichloro-pyridine-N-oxide with $H_2O_2$. This compound is treated at 135° C. in an autoclave with an excess of $Na_2SO_3$, resulting in the sodium salt of pyridine-3,5-disulfonic acid-N-oxide which is reduced by $NaBH_4$ to yield the sodium salt of pyridine-3,5-disulfonic acid. The disalt is alkylated with methyl methanesulfonate to yield sodium [3,5-disulfonato-1-methyl-pyridinium].

Example 3

3,5-pyridine-dicarboxamide is made from the action of $NH_3$ on dimethyl-pyridine-3,5-dicarboxylate. This diamide is quaternarized with dimethyl sulfate and treated with a solution of cyanogen bromide in acetonitrile in the presence of imidazole. The result is the imidazolium salt of N,N'-dicyano-1-methyl-pyridinium-3,5 dicarboxamide.

What is claimed:

1. A salt of formula (I)

$$X^- M^+ \qquad (I)$$

wherein $M^+$ is selected from the group consisting of Li, Na, K, an ammonium, a phosphonium, an imidazolium, a pyridinium, and a pyrazolium; and wherein $X^-$ is an anion formed from covalent linking of two negative moieties to a positive onium-type core and $X^-$ is selected from the group consisting of

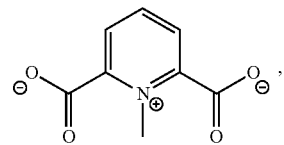

2,6-dicarboxy-1-methyl-pyridinium

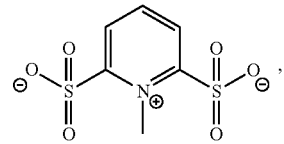

2,6-disulfonato-1-methyl-pyridinium

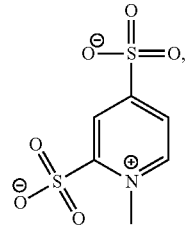

1,4-disulfonato-1-methyl-pyridinium

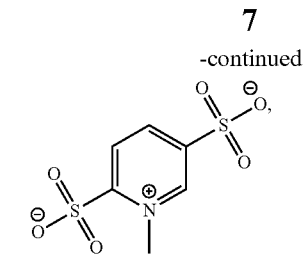

1,5-disulfonato-1-methyl-pyridinium

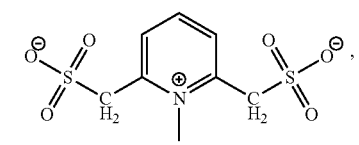

2,6-bis (sulfonato-methyl)-1-methyl-pyridinium

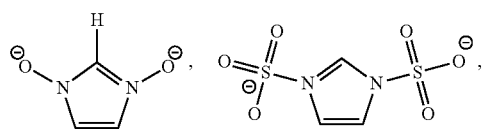

1,3 dioxyimidazolium     1,3 sulfonatoimidazolium

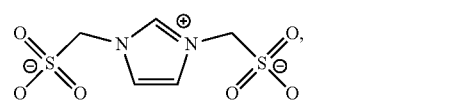

1,3-bis (sulfonato-methyl)-imidazolium

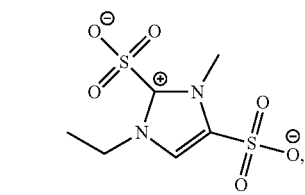

1-ethyl-2-methyl-2,4-bis sufonatoimidazolium

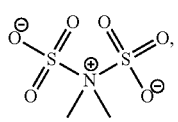

bis-sulfonato-dimethyl ammonium

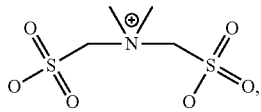

bis (sulfonato-methyl)-dimethyl ammonium

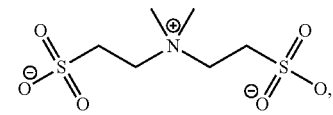

bis (sulfonato-2-ethyl)-dimethyl ammonium

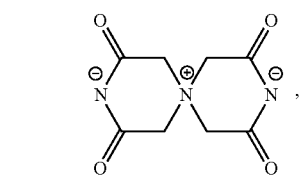

spiro-3,5,3'5'tetraoxa-4,4' diaza-bis-piperidinium

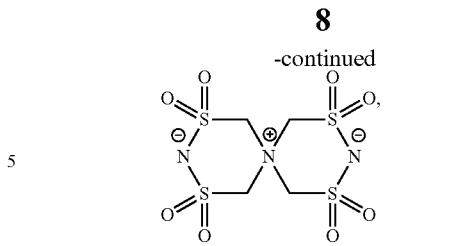

spiro-3,5,3'5'tetrathia-4,4' diaza-bis-piperidinium, 3,5,5,5'octaoxide

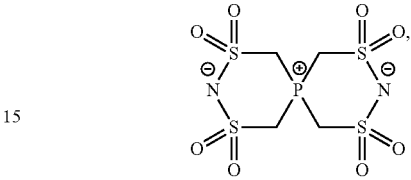

spiro-3,5,3'5'tetrathia-4,4' diaza-bis-phospa-piperidinium, 3,5,5,5'octaoxide

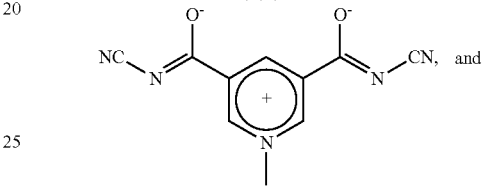

N,N'-dicyano-1-methyl-pyridinium-3,4 diccarboxamide

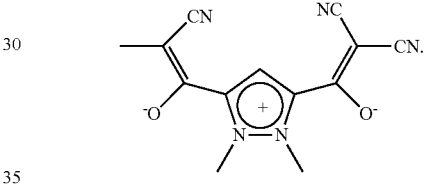

3,5-(dimalono-carbonyl)-1,2-dimethyl-pyrazolium

2. A electrolyte comprising at least one salt according to claim 1 dissolved in a polar solvent, a solvating polymer or a mixture thereof.

3. An electrolyte of claim 2 wherein the polar solvent is selected from the group consisting of linear and cyclic carbonates, ethers including mono-, di-, tri- and tetra-ethylene glycol di-methyl ether, tetrahydrofurane, γ-butyrolactone, vinylene carbonate, tetraalkyl sulfonamides, and mixtures thereof.

4. An electrolyte of claim 2 wherein the solvating polymer is selected from the group consisting of poly(ethylene oxide), polyacrylamide, poly(ethylene glycol) diacrylate or dimethacrylate, poly(methoxy ethylene glycol) monoacrylate or methacrylate, their random or block polymers with styrene, and a polyether comprising at least 60% of oxyethylene units.

5. A battery comprising:
   a positive electrode; and
   a negative electrode; and
the electrolyte of claim 2 further containing lithium or sodium ions.

6. The battery of claim 5 wherein the negative electrode is selected from the group consisting of metallic lithium, a lithium intercalation derivative of soft or hard carbons, graphite, a lithium-aluminum alloy, a lithium silicon alloy and $Li_4Ti_5O_{12}$.

7. A battery of claim 5 wherein the positive electrode comprises $LiFe_{1-x}Mn_xPO_4$ wherein $0 \leq x \leq 1$, $LiFeSO_4F$, $Li_yMn_2O_4$ wherein $0 \leq y \leq 1$, $Li_zCoO_2$ wherein $0 \leq z \leq 0.6$ or mixtures thereof.

8. A battery of claim 5 wherein the negative electrode comprises sodium, a sodium intercalation derivative of hard carbons, a sodium-lead alloy or $Na_{2+q}Ti_3O_7$ wherein $0 \leq q \leq 2$.

9. A battery according to claim 5 characterized in that the positive electrode comprises $Na_rFePO_4$, ($0 \leq r \leq 1$) or $Na_{2-s}FePO_4F$ ($0 \leq s \leq 1$) or $Na_{1-t}MnO_2$ ($0 \leq t \leq 1$) and mixtures thereof.

* * * * *